(12) United States Patent
Weinstein

(10) Patent No.: US 6,651,816 B2
(45) Date of Patent: Nov. 25, 2003

(54) ANTIHISTAMINE/DECONGESTANT REGIMENS FOR TREATING RHINITIS

(76) Inventor: Robert E. Weinstein, 177 Commonwealth Ave., Boston, MA (US) 02116

( * ) Notice: Subject to any disclaimer, the term of this patent is extended or adjusted under 35 U.S.C. 154(b) by 46 days.

(21) Appl. No.: 09/849,579

(22) Filed: May 4, 2001

(65) Prior Publication Data

US 2002/0162769 A1 Nov. 7, 2002

(51) Int. Cl.[7] .............................................. B65D 83/04
(52) U.S. Cl. ...................................... 206/534; 206/538
(58) Field of Search ................................. 206/528, 530, 206/531, 534, 538, 539; 424/457, 468; 604/890.1, 50, 54

(56) References Cited

U.S. PATENT DOCUMENTS

| | | | | |
|---|---|---|---|---|
| 4,295,567 A | * | 10/1981 | Knudsen ..................... | 206/534 |
| 5,848,976 A | * | 12/1998 | Weinstein .................... | 600/556 |
| 6,051,585 A | * | 4/2000 | Weinstein et al. ........... | 514/335 |
| 6,114,346 A | * | 9/2000 | Harris et al. ................. | 514/290 |
| 6,270,796 B1 | * | 8/2001 | Weinstein .................... | 424/457 |
| 6,372,197 B1 | * | 4/2002 | Rubin .......................... | 424/45 |
| 6,432,972 B2 | * | 8/2002 | Salmun et al. .............. | 514/291 |
| 6,469,009 B1 | * | 10/2002 | Van De Venne et al. ... | 514/653 |

* cited by examiner

*Primary Examiner*—Shian Luong
(74) *Attorney, Agent, or Firm*—Robert R. Deleault, Esq.; Mesmer & Deleault, PLLC

(57) ABSTRACT

A prepackaged, therapeutic regimen includes a non-sedating first dosage unit that includes a nasal decongestant, a second dosage unit that includes an antihistamine and an attenuated dosage of nasal decongestant, indicia for distinguishing between the first and second dosage units, administration instructions that teach the coordinated use of the first and second dosage units, and a pharmaceutical dispensing container containing the first and second dosage units and incorporating the indicia and coordinating instructions.

14 Claims, 2 Drawing Sheets

ANTIHISTAMINE/DECONGESTANT REGIMENS FOR TREATING RHINITIS

BACKGROUND OF THE INVENTION

1. Field of the Invention

The present invention relates to prepackaged therapeutic regimens for the symptomatic treatment of individuals with rhinitis, which combine decongestant and antihistamine medications in a manner to avoid daytime sedation and minimize stimulation from decongestants.

2. Description of the Prior Art

Rhinitis refers to an inflammatory disorder of the nasal passages. The symptoms of rhinitis typically consist of sneezing, rhinorrhea, nasal congestion, and increased nasal secretions. Failure of treatment of rhinitis may lead to other disorders including infection of the sinuses, ears and lower respiratory tract.

Two types of oral medication are commonly used to treat rhinitis: decongestants and antihistamines. Decongestants and antihistamines differ in mechanism of action, therapeutic effects and side effects. It is common practice to combine the use of these two to bring about more complete symptom relief of rhinitis than with either entity alone.

Decongestants act to constrict vessels in the nasal mucus membranes and thereby decrease tissue swelling and nasal congestion. They are known to open congested nasal airways more effectively than antihistamines. Examples of oral nasal decongestants include pseudoephedrine and phenylephrine. Nasal decongestants are adrenalin-like, and therefore stimulatory. Their therapeutic effect may be accompanied by side effects of irritability, hyperactivity, and restlessness. At night they are known to produce insomnia. Susceptibility to the stimulatory effect of decongestants is known to vary widely among individuals. Some individuals tolerate these agents well, while others encounter varying degrees of intolerance. In some instances, individuals are able to tolerate the stimulatory effects while active, as during the day, but not a night, when they interfere with sleep.

Histamine is a mediator released from cells that line the walls of the nasal mucous membranes (mast cells). When released, histamine is known to bind to local receptors and cause sneezing, nasal itching, swelling of the nasal membranes, and increased nasal secretions. Antihistamines block the binding of histamine to histamine receptors in the nasal membranes and preempt the precipitation of these symptoms by histamine release. Although individuals typically take antihistamines after symptoms occur, it is more desirable to dose antihistamine so as to effect therapeutic availability in anticipation of the peak times of histamine release, typically in the early morning hours in allergic rhinitis. Antihistamines are known to be sedating. To improve upon this, newer antihistamines with no or little sedation have been developed.

Decongestants and antihistamines have been formulated into single dosage units to offer more complete relief of rhinitis symptoms than therapy with either component alone. The incorporation of stimulating decongestant and sedating antihistamine into a single dosage unit represents an attempt to balance stimulation and sedation of the components. As noted, individuals vary in their susceptibility to side effects, and some individuals experience irritability, sedation, or both when taking these combinations. Formulations containing decongestant and sedating antihistamine are exemplified by:

CHLOR-TRIMETON® 4 hour Allergy/Decongestant which contains 4 mg of chlorpheniramine (sedating antihistamine) and 60 mg pseudoephedrine sulfate (stimulating decongestant), and which is recommended to be taken every 4–6 hours (½ this dosage for children 6 to under 12).

BROMFED® Tablets which contains 4 mg of brompheniramine (sedating antihistamine) and 60 mg pseudoephedrine sulfate (stimulating decongestant), and which is recommended to be taken every 4–6 hours (½ this dosage for children 6 to under 12).

BENADRYL® Allergy Decongestant Tablets which contains 25 mg of iphenhydramine hydrochloride (sedating antihistamine) and 60 mg seudoephedrine sulfate (stimulating decongestant), and which is recommended to be taken by adults and children over 12 years of age every 4–6 hours, not to exceed 4 tablets in 24 hours.

TAVIST-D® Tablets which contains 1.34 mg clemastine fumarate (sedating antihistamine) and 75 mg phenylpropanolamine hydrochloride (stimulating decongestant), and which is recommended to be taken every 12 hours (adults and children over 12 years of age only).

Formulations have also been commercialized which incorporate a decongestant and a non-sedating antihistamine into a single dosage unit. Such combinations would be expected, in general, to be more stimulating than combinations, which employ a sedating antihistamine that might counter the effects of stimulation caused by the decongestant. Examples of such formulations include:

CLARITIN-D® 24 HOUR Extended-Release Tablets which contains 10 mg loratidine (antihistamine) and 240 mg pseudoephedrine hydrochloride (decongestant) and which is recommended to be taken every 24 hours (adults and children over 12 years of age).

ALLEGRA-D™ containing 60 mg fexofenadine (non-sedating antihistamine) and 120 mg pseudoephedrine hydrochloride (stimulating decongestant) and which is recommended for every 12 hours (adults and children over 12 years of age).

All of the single dosage units described are instructed, by their manufacturers, for use around the clock. U.S. Pat. No. 4,295,567 (Knudsen) teaches a packaged regimen which provides and instructs use of sedating antihistamine only at night in order to avoid daytime sedation from antihistamine. Knudsen does not address the stimulatory side- effects of decongestants. Particularly, Knudsen contains no teaching to avoid the stimulating side effects from decongestants that can occur when antihistamines and decongestants are used together.

Regimens have been commercialized which incorporate a decongestant for daytime and not for nighttime. An example of one such prepackaged regimen is SYN-RX™, which contains 60 mg pseudoephedrine HCL and 600 mg Guaifenesin in the day formulation and 600 mg of guaifenesin in the nighttime formulation. These regimens avoid stimulation from decongestant at night, however lack antihistamine. Further, they neither contain medication which would be effective for rhinitis symptoms at night, nor anticipate peak symptoms of rhinitis in the morning hours on awakening.

It is well known that individuals with rhinitis utilize antihistamines and decongestants together hundreds of millions of times a year, often encountering undesired side effects. While it is desirable to take advantage of the therapeutic benefits of decongestant medications for rhinitis, there is a present need for regimens which advantageously use antihistamines and decongestants in a manner to minimize the side effects of decongestants as well as antihistamines, particularly regimens which fulfill individual needs in accord with individual variations in susceptibility to side effects of decongestants.

Prevention of medication error is a considerable problem and is improved with measures to establish simplicity, reduce confusion, and increase convenience. The proposed use of a multiplicity of dosage units as a regimen may be associated with dosage units being confused with each other, inadvertently switched, lost, misplaced, or ignored. Another problem associated with treatment using a plurality of units is the lack of indicia which distinguish the dosage units from each other and signify and verify their use together. Yet another problem is the lack of readily available instructions for coordinating the medications. Individuals are known to lose instructions issued separate from medication in its immediate container. Haphazard selection and organization of medications can result in treatment failure and in the patient's requiring additional medical attention involving time, expense and personnel costs and effort to instruct the patient and organize therapy. Cost factors and outcomes are being carefully considered in the current medical climate. Improvements in organization and teaching including devices and methods which would help patients be more cognizant of their proper therapeutic requirements are considered desirable in view of limitations in time and costs for medical personnel. Successful therapy for rhinitis is less costly than unsuccessful treatment that eventuates in complications or multiple clinic visits.

SUMMARY OF THE INVENTION

It is an object of the present invention to provide a rhinitis regimen that utilizes both decongestants and antihistamines, which is non-sedating during the day, and which minimizes stimulation from decongestant.

It is a further objective of the present invention to provide users with a suitable antihistamine-decongestant regimen in accord with each individual's susceptibility to the stimulatory effects of decongestants, the spectrum of such susceptibility being known to vary considerably between individuals.

It is another objective of the present invention to provide a user with such regimens packaged together with coordinated instructions which teach the use of the incorporated dosage units as a regimen, such packaging being performed by a pharmaceutical manufacturer.

The devising of such formulations and instructions for the use of such formulations requires pharmaceutical expertise and requires understanding of the actions, side effects and pharmacokinetics of antihistamines, decongestants, and other formulated components as well determination of the suitability of the components use together. It is therefore another objective of the present invention to provide a user with expertly devised regimens.

It is yet another objective of present invention to provide a method and device for organizing, storing and coordinating said regimens for the purpose of convenience and reducing error in using such regimens by providing such regimens in a prepackaged container that incorporates coordinating indicia and coordinating instructions.

It is a further object to increase the convenience of using a regimen of different dosage units for rhinitis by organizing such regimens in a unitary package.

It is still a further objective of the present invention to provide regimens which provide dosing of antihistamine in accordance with its kinetics so as to achieve significant histamine receptor binding in the morning hours, at the conventional time of awakening, when such scheduling is typically desired.

Other objects of the present invention will become apparent in light of the following drawings and detailed description of the invention.

DETAILED DESCRIPTION OF THE PREFERRED EMBODIMENT

Figure 1:
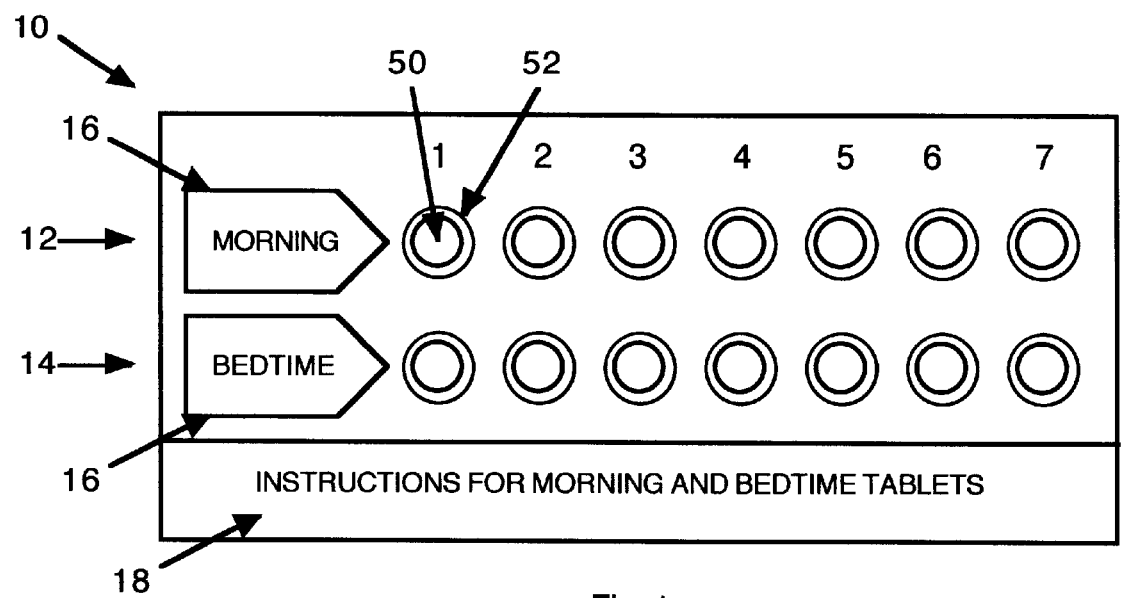
FIG. 1 is a plan view of one embodiment of the present invention.

The preferred embodiment(s) of the present invention is illustrated in FIGS. 1–4. The present invention teaches a prefilled, unifying dispensing container containing at least two different dosage units for the treatment of rhinitis, and containing indicia for distinguishing the dosage units and signifying their use together, and coordinated instructions for their use together. It is to be understood that either single or multiple doses of each dosage units are contained. The dosage units may be in the form of tablet, pill, capsule, caplet, powders, liquids, gels, some of which may require reconstituting, or any generally recognized oral form of medication.

Referring to the drawings, it will be understood that while preferred embodiments of the invention have been illustrated and described, the invention is not limited to such embodiments. Changes and additions may be made therein and thereto without departing from the spirit of the invention.

Figure 2:
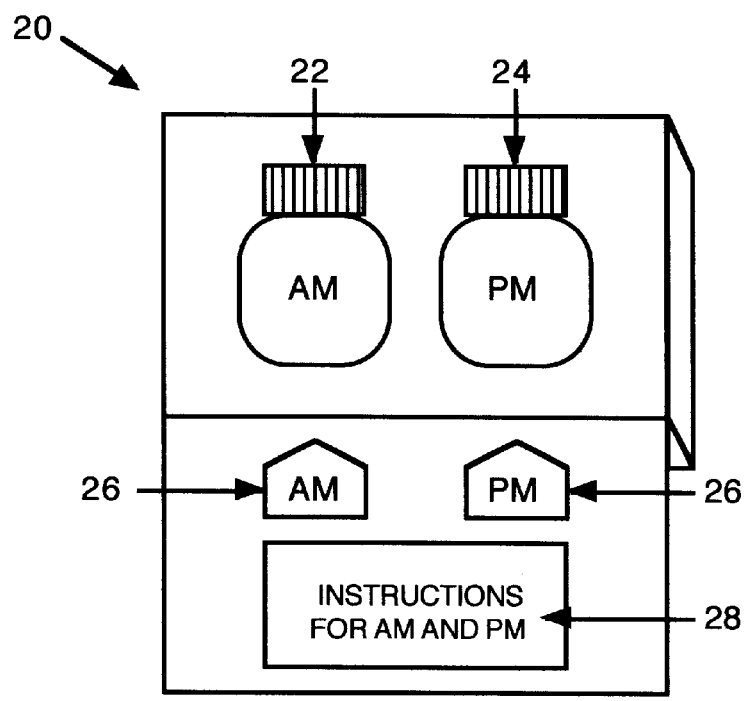
FIG. 2 is top view of another embodiment of the present invention.
Figure 3:
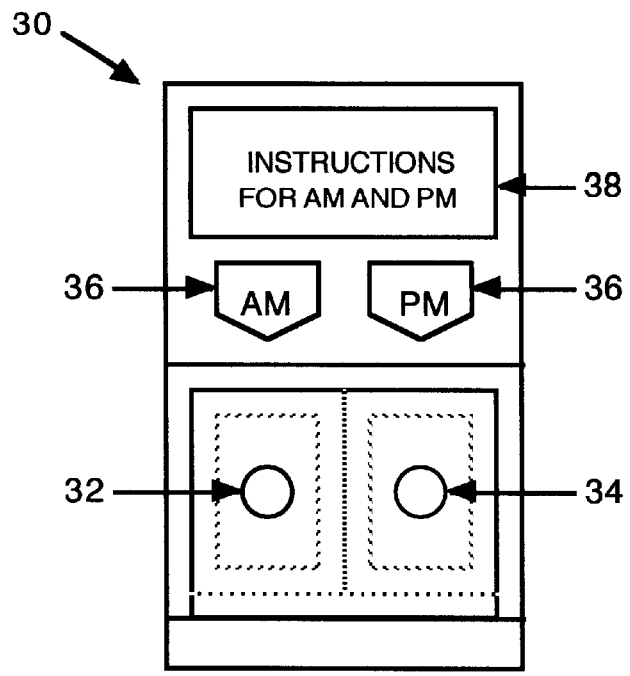
FIG. 3 is plan view of a third embodiment of the present invention.
Figure 4:
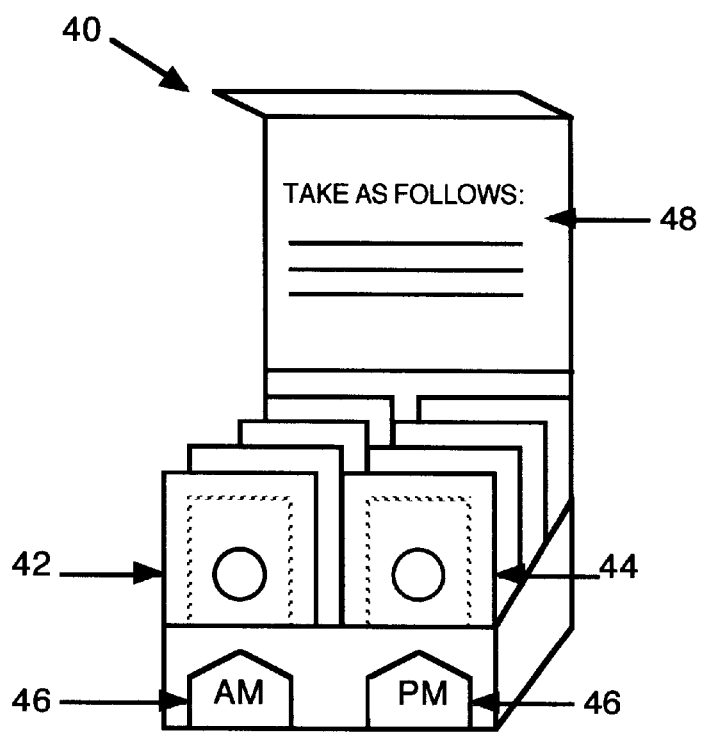
FIG. 4 is front view of a forth embodiment of the present invention.

Embodiments of the unifying container of the preferred invention are depicted in FIGS. 1–4. FIG. 1 depicts a support package 10 containing multiple dosages of two different dosage units 12, 14 in tablet form 50 in blister packaging 52. FIG. 2 depicts a support package 20 which houses two modules in the form of bottles 22, 24 containing different dosage units, which can be either in liquid form or in solid form. FIG. 3 depicts a support package 30 with a single dosage unit 32 for morning and a single different dosage unit 34 for night. FIG. 4 depicts a support package 40 which is manufactured to house a multiplicity of daytime modules in the form of pouches 42 and a multiplicity of nighttime modules in the form of pouches 44. In each of the four depicted configurations, the support package has specific provision for supporting said dosage units in physical accord with indicia 16,26,36,46 of FIGS. 1–4, respectively.

The indicia manufactured with the support package distinguishes between the dosage units by means of wording, color, shape symbol, or other means known in the art. The indicia, by their presence, also indicate the suitability of said dosage units for use with each other. The support package also incorporates coordinated administration instructions 18,28,38,48 of FIGS. 1–4, respectively, which also indicate the suitability of the dosage units for use with each other, and instruct coordination of the dosage units as a regimen.

Although the embodiments specifically described herein have two medicament housings, packaging containing other numbers of housings is also within the scope of this invention. The packaging may be adapted by widening the packaging and increasing the number of housings and indicia. Additionally, the packaging may be in any geometric configuration.

The packaging contains combinations of medications, which include nasal decongestants and antihistamines that comprise a regimen for treating rhinitis. Specifically, the packaged medication is comprised of at least two dosage units, a non-sedating dosage unit for administration during the day, and a dosage unit, which is non-stimulatory in accord with the susceptibility of the user, for use at night. The package also contains instructions for taking the dosage units as a regimen. It is to be understood that the nighttime dosage unit, at least, contains a lesser amount of decongestant as compared to the aforementioned conventional decongestant-antihistamine dosage units. It is considered that in the case of a package intended for over-the-counter sales, a comparison between the amount of decongestant to conventional dosing is provided by the instructions, indicia, or both in a manner which would allow a user to estimate the degree of stimulation which might be expected. In the case of a package intended for prescription, however, the prescribing provider would be expected to be able to assess the stimulatory qualities of such regimens on behalf of the user, and the inclusion of such a comparison within the package is optional.

The daytime dosage unit may be formulated to contain non-sedating antihistamine, and/or decongestant, but not sedating antihistamine. The decongestant may be in conventional or attenuated quantity. The nighttime dosage unit may be formulated to contain sedating or nonsedating antihistamine, and, if containing decongestant, contains an attenuated quantity in comparison to conventional dosing. The terms "daytime" is intended to be synonymous with a time when sedation is considered undesirable, such as time of awakening, and the term "nighttime" to be synonymous with times when stimulation would be undesired, such as times of sleeping, as well as daytime and nighttime literally, in that such times vary in accordance with the schedule of individuals. The regimen is devised using dosage units, which are favorable for use with each other, especially with regard to their pharmacokinetic and therapeutic characteristics. The following are examples of regimens according to the present invention:

EXAMPLE 1

The following regimen is suggested for an individual who is considered to be moderately susceptible to the stimulating side-effects of decongestants:

Daytime dosage: 90 mg pseudoephedrine hydrochloride in 12 hour time-release formulation, and 5 mg loratidine (to be taken in the morning), and Bedtime dosage: 60 mg pseudoephedrine hydrochloride in 12 hour time-release formulation, and 5 mg loratidine (to be taken at bedtime).

This regimen employs the stimulating decongestant pseudoephedrine hydrochloride and the non-sedating antihistamine loratidine. The conventional 12–hour dosing of 120 mg of pseudoephedrine has been illustrated by the aforementioned examples of single dosage unit antihistamine-decongestant combinations. As noted, stimulatory side effects are known to occur with conventional dosing, and some individuals are more susceptible to side effects than others. This regimen utilizes a morning dosing to 90 mg of pseudoephedrine, instead of the conventional 120 mg, and a bedtime dosing to 60 mg, one-half of the conventional 120 mg, to achieve therapeutic effects to address side effects in an individual considered to have a moderate degree of susceptibility. Consideration of susceptibility and therefore appropriateness of this regimen may be based upon self-assessment of prior experience, or assessment by a caregiver. Methods for time-release formulation of pseudoephedrine are well known in the art. Avoidance of daytime sedation is considered important in regimens of the present invention, and is avoided by the employment of the non-sedating antihistamine, loratidine. Half of the daily loratidine dose is given at bedtime to assure significant receptor binding in the morning.

EXAMPLE 2

The following regimen is considered appropriate for an individual who is moderately susceptible to the stimulating side-effects of decongestants, and particularly susceptible to insomnia from decongestants at night:

Daytime dosage: 90 mg pseudoephedrine hydrochloride in 12 hour time-release formulation (to be taken in the morning), and Nighttime dosage: 30 mg pseudoephedrine hydrochloride in 12 hour time-release formulation, and 4 mg of chlorpheniramine (to be taken at bedtime).

In this example, the total 24 hour dose of 120 mg of pseudoephedrine is one-half that of conventional dosing. By reducing the morning dose of pseudoephedrine to 90 mg, instead of the conventional 120 mg, and the bedtime dose to 30 mg, instead of the conventional 120 mg, a balance between therapeutic and side effects might be achieved in an individual susceptible to stimulatory side-effects, particularly insomnia. The potential for nighttime stimulation from pseudoephedrine is further diminished by the inclusion of the sedating antihistamine, chlorpheniramine in the nighttime formulation. Dosing of antihistamine at bedtime favors binding by histamine receptors in the morning, when such binding is typically most desired.

EXAMPLE 3

60 mg pseudoephedrine sulfate in a 12-hour time release formulation, and 60 mg of fexofenadine (to be taken in the morning), and 60 mg of fexofenadine (to be taken in the evening).

For an individual known to be prone to insomnia with decongestants, limitation of pseudophedrine dosing to the day, in this example, avoids stimulation and insomnia at night. Dosing of one half of the conventional daytime dosage of 120 mg of pseudoephedrine might suit an individual who is susceptible to its side effects but able to tolerate a decreased dosage in order to gain therapeutic benefit. Use of the non-sedating antihistamine fexofenadine avoids daytime sedation compared to sedating antihistamine. The 12-hour duration of antihistaminic activity of fexofenadine requires daytime dosing to achieve an effective daytime combination of antihistamine and decongestant. Binding of fexofenadine to the histamine receptors in the morning is expected with its bedtime dosing.

In addition to antihistamines and decongestants, additional therapeutic ingredients for the treatment of rhinitis may be formulated if desired. For example, analgesics, anticholinergic agents, and inhibitors of allergic mediators other than histamine, such as those generated by the arachadonic acid pathways, may be considered for inclusion in such formulations and are within the scope of this invention.

These examples do not constitute an exhaustive list of potential combinations, and variations and modifications may be made by those of ordinary skill in the art. Those of skill in the art may also recognize modifications to these presently disclosed embodiments. These variations and modifications are meant to be covered by the spirit and scope of the present claims.

What is claimed is:

1. A prepackaged therapeutic regimen comprising:
   (a) a non-sedating first dosage unit, which includes a nasal decongestant:
   (b) a second dosage unit which includes an antihistamine having an absence of any decongestant effect and an attenuated dosage of nasal decongestant;
   (c) indicia for distinguishing between said first and said second dosage units;
   (d) administration instructions which teach the coordinated use of said dosage units as a rhinitis regimen, such that said first dosage unit is instructed for daytime administration, and said second dosage unit is instructed for nighttime administration; and
   (e) a pharmaceutical dispensing container prefilled with said dosage units, and incorporating said indicia, and said coordinating instructions.

2. The prepackaged therapeutic regimen of claim 1 wherein said antihistamine is non-sedating.

3. The prepackaged therapeutic regimen of claim 1 wherein said antihistamine is sedating.

4. The prepackaged therapeutic regimen of claim 1 wherein said decongestant is pseudoephedrine.

5. The prepackaged therapeutic regimen of claim 1 wherein said dispensing container is a blister pack.

6. The prepackaged therapeutic regimen of claim 1 wherein said dispensing container incorporates bottles containing solid medications.

7. A prepackaged therapeutic regimen comprising:
   (a) a non-sedating first dosage unit, which includes a nasal decongestant in an attenuated dosage:
   (b) a second dosage unit which includes an antihistamine having an absence of any decongestant effect and an attenuated dosage of nasal decongestant;
   (c) incidia for distinguishing between said first and said second dosage units;
   (d) administration instructions which teach the coordinated use of said dosage units as a rhinitis regimen, such that said first dosage unit is instructed for daytime administration, and said second dosage unit is instructed for nighttime administration; and
   (e) a pharmaceutical dispensing container prefilled with said dosage units, and incorporating said indicia, and said coordinating instructions.

8. The prepackaged therapeutic regimen of claim 7 wherein said antihistamine is non-sedating.

9. The prepackaged therapeutic regimen of claim 7 wherein said antihistamine is sedating.

10. The prepackaged therapeutic regimen of claim 7 wherein said decongestant is pseudoephedrine.

11. The prepackaged therapeutic regimen of claim 7 wherein said dispensing container is a blister pack.

12. The prepackaged therapeutic regimen of claim 7 wherein said dispensing container incorporates bottles containing solid medications.

13. A method for rhinitis treatment comprising the steps of:
   (a) formulating a rhinitis treatment regimen comprising a non-sedating first dosage unit, which includes a nasal decongestant and a second dosage unit which includes an antihistamine having an absence of any decongestant effect and an attenuated dosage of nasal decongestant;
   (b) providing indicia for distinguishing between said first and said second dosage units;
   (c) providing administration instructions for the coordinated use of said dosage units; and
   (d) prefilling a pharmaceutical dispensing container with said dosage units, and incorporating said indicia, and said coordinating instructions for a user.

14. A method for rhinitis treatment comprising the steps of:
   (a) formulating a rhinitis treatment regimen comprising a non-sedating first dosage unit, which includes a nasal decongestant in an attenuated dosage and a second dosage unit which includes an antihistamine having an absence of any decongestant effect and an attenuated dosage of nasal decongestant;
   (b) providing indicia for distinguishing between said first and said second dosage units; (c)
   providing administration instructions for the coordinated use of said dosage units; and
   (d) prefilling a pharmaceutical dispensing container with said dosage units, and incorporating said indicia, and said coordinating instructions for a user.

* * * * *